US010835474B2

(12) United States Patent
Lange et al.

(10) Patent No.: US 10,835,474 B2
(45) Date of Patent: Nov. 17, 2020

(54) AGENT AND METHOD FOR THE TEMPORARY SHAPING OF KERATINOUS FIBERS

(71) Applicant: Henkel AG & Co. KGaA, Duesseldorf (DE)

(72) Inventors: Julia Bibiane Lange, Bad Bramstedt (DE); Rene Scheffler, Ellerau (DE); Diane Metten, Hamburg (DE); Cyrielle Martinez, Hamburg (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 90 days.

(21) Appl. No.: 15/843,019

(22) Filed: Dec. 15, 2017

(65) Prior Publication Data
US 2018/0168989 A1    Jun. 21, 2018

(30) Foreign Application Priority Data
Dec. 19, 2016    (DE) .......................... 10 2016 225 465

(51) Int. Cl.
| *A61Q 5/06* | (2006.01) |
| *A61K 8/81* | (2006.01) |
| *A61K 8/86* | (2006.01) |
| *C08L 33/00* | (2006.01) |
| *C08L 33/02* | (2006.01) |

(52) U.S. Cl.
CPC .............. *A61K 8/8152* (2013.01); *A61K 8/86* (2013.01); *A61Q 5/06* (2013.01); *C08L 33/00* (2013.01); *C08L 33/02* (2013.01); *A61K 2800/594* (2013.01)

(58) Field of Classification Search
None
See application file for complete search history.

(56) References Cited

U.S. PATENT DOCUMENTS

| 8,741,273 B2 | 6/2014 | Knappe et al. |
| 10,583,077 B2 | 3/2020 | Lange et al. |
| 2018/0055756 A1 | 3/2018 | Lange et al. |

FOREIGN PATENT DOCUMENTS

| DE | 102007053954 A1 | 5/2009 | |
| DE | 102009001978 A1 | 10/2010 | |
| DE | 102015204146 A1 * | 9/2016 | ............... A61Q 5/06 |
| DE | 102015204148 A1 * | 9/2016 | ............... A61Q 5/06 |
| DE | 102015204149 A1 | 9/2016 | |
| DE | 102015204150 A1 | 9/2016 | |
| WO | 2016142009 A1 | 9/2016 | |
| WO | 2016142013 A1 | 9/2016 | |

OTHER PUBLICATIONS

Intellectual Property Office, Search Report under Section 17(5) for United Kingdom Patent Application No. GB1721122.8 dated Jul. 13, 2018.

* cited by examiner

*Primary Examiner* — Jyothsna A Venkat
(74) *Attorney, Agent, or Firm* — Lorenz & Kopf, LLP

(57) ABSTRACT

The present disclosure relates to a cosmetic preparation for the temporary shaping of hair, which comprises a combination of two specific copolymers. The cosmetic composition provides an extremely good hold.

7 Claims, No Drawings

AGENT AND METHOD FOR THE TEMPORARY SHAPING OF KERATINOUS FIBERS

CROSS-REFERENCE TO RELATED APPLICATION

This application claims priority to German Patent Application No. 10 2016 225 465.0, filed Dec. 19, 2016, which is incorporated herein by reference in its entirety.

TECHNICAL FIELD

The present disclosure relates to a cosmetic composition for hair setting or for temporarily shaping keratinous fibers, in particular human hair, wherein the composition contains a combination of two specific crosslinked copolymers.

BACKGROUND

The temporary design of hairstyles for a longer period of time of up to several days normally requires the use of setting active ingredients. Therefore, hair treatment agents that temporarily shape the hair play a role. Corresponding agents for temporary shaping normally contain synthetic polymers and/or waxes as a setting active ingredient. Agents aiding the temporary shaping of keratinous fibers can normally be packaged, for instance, as hairspray, hair wax, hair gel or mousse. One feature of an agent for the temporary shaping of hair, also referred to hereinafter as a styling agent, is giving the treated fibers in the newly modeled shape—i.e. a shape impressed on the hair—the strongest possible hold. This is also referred to as a strong hairstyle hold or a high degree of hold of the styling agent. The hairstyle hold is determined by the type and amount of setting active ingredients used, wherein the other components of the styling agent can also have an influence. In addition to a high degree of hold, the styling agent must fulfill a series of additional requirements. They can be roughly divided in to characteristics on the hair, characteristics of the respective formulation, e.g. characteristics of the foam, gel or sprayed aerosol, and characteristics relating to the handling of the styling agent. This includes, in particular, moisture resistance, low stickiness (tack) and a balanced conditioning effect. Furthermore, a styling agent can be universally applicable for all hair types, insofar as possible, and mild to the hair and skin. A plurality of synthetic polymers has already been developed as setting active ingredients, which can be used in styling agents, in order to satisfy the various requirements. The polymers can be divided into cationic, anionic, nonionic and amphoteric setting polymers. Ideally, the polymers create a polymer film when used on the hair, which lends the hairstyle a strong hold and is sufficiently flexible in order to reduce breaking under stress. If the polymer film is too brittle, flakes form, i.e. residue, which detach during movement of the hair and give the impression that the user of the styling agent concerned has dandruff. Similar problems arise when waxes are used as a setting active ingredient in the styling agent. If the styling agent is a gel or a paste, the polymers may also have thickening properties.

Acrylate copolymers with two or more structural units are known anionic polymers that are used in hair setting products. Certain copolymers of this kind with the trade designation Aculyn® 33A (INCI: Acrylates Copolymer) and the use thereof in cosmetic compositions for the temporary shaping of keratinous fibers are described in the German application DE 10 2007 053 954 A1.

Additional anionic polymers that are used in hair setting products are crosslinked anionic amphiphilic polymers that contain a (meth) acrylic acid unit and a (meth)acrylic acid oxyalkylene alkyl ester unit. Such polymers are described in the international patent application WO 2016/142013 A1 and are commercially available, for example, under the name BALANCE® RTF (INCI: Acrylates/Ceteareth-20 Methacrylate Crosspolymer). In styling products, this polymer essentially has the task of a thickening agent and film former.

BRIEF SUMMARY

In accordance with an exemplary embodiment, disclosed is a cosmetic composition for the temporary shaping of keratinous fibers, includes: (a) at least one acrylate copolymer (a), which is composed of at least one of the following monomer units: (a1) at least one (meth)acrylic acid unit, (a2) at least one (meth)acrylic acid ester unit and at least one crosslinked acrylate copolymer (b) differing from the copolymer (a), which of at least one of the following structural units (b1) and (b2):

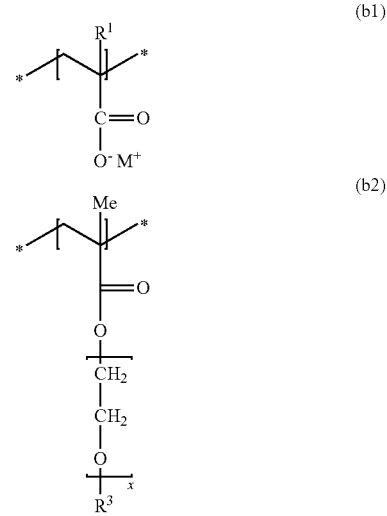

wherein $R^1$ denotes a hydrogen atom or a methyl group, $R^3$ denotes a $(C_8\text{-}C_{30})$-alkyl group, $M^+$ denotes a physiologically tolerated cation and x denotes an integer from about 5 to about 35.

DETAILED DESCRIPTION

The following detailed description is merely exemplary in nature and is not intended to limit the disclosure or the application and uses of the subject matter as described herein. Furthermore, there is no intention to be bound by any theory presented in the preceding background or the following detailed description.

The present disclosure addresses the problem of providing additional polymer combinations, which are exemplified by good film-forming and/or setting properties, have a very high degree of hold without the need to dispense with flexibility and good moisture resistance—particularly sweat and water resistance—and are also suitable for production of stable viscous and stable transparent cosmetic compositions. In particular, currently available styling agents can be improved, because a good combination of stiffness and long-term hold (high humidity curl retention) is not always sufficiently guaranteed. Therefore, the present disclosure addresses the problem of preparing such styling agents that provide the aforementioned properties, particularly with regard to good stiffness and a good, long-term hold.

As contemplated herein, this was achieved by employing a combination of two specific anionic copolymers.

The present application provides:

1. A cosmetic composition for the temporary shaping of keratinous fibers, which contains:
(a) at least one acrylate copolymer (a), which is composed of at least one of the following monomer units:
 (a1) at least one (meth)acrylic acid unit,
 (a2) at least one (meth)acrylic acid ester unit
and
a) at least one crosslinked acrylate copolymer (b) differing from the copolymer (a), which includes at least one of the following structural units (b1) and (b2):

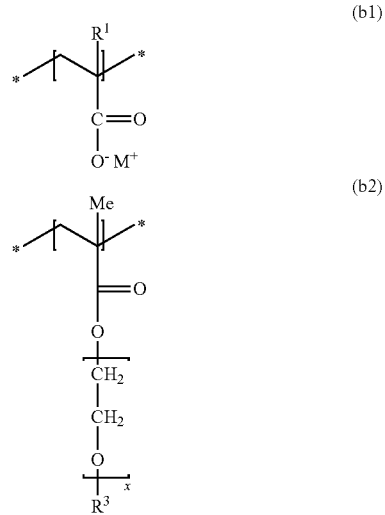

wherein
$R^1$ denotes a hydrogen atom or a methyl group,
$R^3$ denotes a $(C_8-C_{30})$-alkyl group,
$M^+$ denotes a physiologically tolerated cation and
x denotes an integer from about 5 to about 35.

2. Cosmetic composition according to paragraph 1, wherein the at least one acrylate copolymer (a) includes at least about 90 wt. %, such as at least about 95 wt. % and for example of at least about 97 wt. % relative to its total weight of the monomers (a1) (meth)acrylic acid unit and (a2) (meth)acrylic acid ester unit.

3. Cosmetic composition in accordance with one of the preceding paragraphs, wherein the acrylate copolymer (a) comprises an acrylic acid ester unit, such as an acrylic acid (C1-4) alkyl ester as a monomer unit (a2).

4. Cosmetic composition according to one of the preceding paragraphs, wherein the composition contains the copolymer (a) in a proportion of from about 0.1 to about 10 wt. %, such as from about 0.5 to about 7.0 wt. %, for example from about 0.7 to about 5.0 wt. %, relative to the total weight of the cosmetic composition.

5. Cosmetic composition in accordance with one of the preceding paragraphs, wherein the anionic copolymer (a) is a copolymer with the INCI designation Acrylates Copolymer, particularly Aculyn® 33 (Rohm & Haas).

6. Cosmetic composition according to one of the preceding paragraphs, wherein the radical $R^1$ in the structural unit (b1) denotes a methyl group.

7. Cosmetic composition according to one of the preceding paragraphs, wherein $R^3$ in the structural unit (b2) of the crosslinked acrylate copolymer (b) denotes a $(C_{12}-C_{20})$-alkyl group, such as a $(C_{14}-C_{20})$-alkyl group and for example a $(C_{16}-C_{18})$-alkyl group.

8. Cosmetic composition according to one of the preceding paragraphs, wherein $R^3$ in the structural unit (b2) of the crosslinked acrylate copolymer (b) denotes a combination of linear $C_{16}$- and $C_{18}$-alkyl groups.

9. Cosmetic composition according to one of the preceding paragraphs, wherein the x in the structural unit (b2) of the crosslinked acrylate copolymer (b) denotes an integer from about 10 to about 24, such as from about 16 to about 22, for example about 20.

10. Cosmetic composition according to one of the preceding paragraphs, wherein the composition contains the anionic copolymer (b) in a proportion of from about 0.1 to about 10 wt. %, such as from about 0.5 to about 7.0 wt. %, for example from about 0.7 to about 5.0 wt. %, relative to the total weight of the cosmetic composition.

11. Cosmetic composition according to one of the preceding paragraphs, wherein the anionic acrylate copolymer (b) is a crosspolymer with the INCI designation Acrylates/Ceteareth-20 Methacrylate Crosspolymer, such as BALANCE® RCF (AkzoNobel).

12. Cosmetic composition according to one of the preceding paragraphs, wherein the anionic copolymer is (a) Aculyn® 33A (Rohm & Haas) and the anionic copolymer is (b) BALANCE® RCF (AkzoNobel).

13. Cosmetic composition according to one of the preceding paragraphs, which, relative to the total weight of the cosmetic composition, contains:
from about 0.1 to about 10 wt. % of the anionic copolymer (a), and
from about 0.1 to about 10 wt. % of the anionic copolymer (b).

14. Cosmetic composition according to one of the preceding paragraphs, containing, relative to the total weight of the cosmetic composition,
from about 0.1 to about 10 wt. % of the anionic copolymer (a), and
from about 0.7 to about 5.0 wt. % of the anionic copolymer (b).

15. Cosmetic composition according to one of the preceding paragraphs, wherein the composition additionally contains at least one copolymer (c) which is different from the copolymers (a) and (b), particularly an anionic or nonionic polymer (c).

16. Cosmetic composition according to one of the preceding paragraphs, exemplified in that it additionally contains, relative to its total weight,
c) polyvinylpyrrolidone and/or vinylpyrrolidone/vinyl acetate copolymer, such as polyvinylpyrrolidone.

17. Cosmetic composition according to point 16, exemplified in that the proportion by weight of the polyvinylpyrrolidone and/or vinylpyrrolidone/vinyl acetate copolymer c) is from about 1.0 to about 10 wt. % of the total weight of the cosmetic composition, such as from about 2.0 to about 8.5 wt. % and for example from about 3.0 to about 7.0 wt. %.

18. Cosmetic composition according to one of the preceding paragraphs, wherein the composition contains water and the proportion by weight of the water of the cosmetic composition is between about 50 and about 95 wt. %, such as between about 60 and about 90 wt. % and for example between about 65 and about 85 wt. %.

19. Cosmetic composition according to one of the preceding paragraphs, wherein the composition is provided as hair gel, hairspray, mousse or hair wax, particularly as hair gel.

20. Use of a cosmetic composition according to one of the paragraphs 1 to 19 for the temporary shaping of keratinous fibers.

21. Use of a cosmetic composition according to one of the paragraphs 1 to 19 for the improvement of the hold of temporarily shaped keratinous fibers.

22. Method for the temporary shaping of keratinous fibers, such as human hair, wherein the cosmetic composition according to one of the paragraphs 1 to 15 is applied to keratinous fibers.

Surprisingly, it was discovered in the context of the present disclosure that a combination of two known components that are already used in styling products can achieve an improved hold of styling products. Other conventionally required properties of styling products, such as moisture resistance, stiffness and low stickiness are retained in the process. Such a good combination of properties was not to be expected even when the individual components are known and was surprising. Experiments showed that the combination of the two components produced a strong overadditive, in other words a synergistic effect with regard to the hold, which is manifested in the 3PB test (3-point bending test).

As contemplated herein, the term keratinous fibers comprises fur, wool and feathers, such as human hair.

The essential components of the cosmetic composition claimed are the copolymer (a) and the crosslinked copolymer (b) differing from copolymer (a).

The cosmetic composition of the present disclosure contains the copolymer (a) and the crosslinked acrylate copolymer (b) in conventional and suitable quantities the styling agent, which can be adjusted for the special application and packaging.

The composition claimed can contain the copolymer (a), for example, in a quantity of from about 0.1 to about 10 wt. % relative to the total weight of the composition claimed. Proportions of the copolymer (a) from about 0.5 to about 7.0 wt. % and from about 0.7 to about 5.0 wt. % are exemplary, specified as the solids content of active substance in the cosmetic composition.

The anionic acrylate copolymer (a) is composed at least of at least one (meth)acrylic acid unit (a1) and at least one (meth)acrylic acid ester unit (a2).

The copolymer (a) can, as contemplated herein, be built up from further monomer units. However, in an exemplary embodiment of the present disclosure, the copolymer (a) consists only of units (a1) and (a2), i.e. it is composed of units derived from these monomer units.

The at least one (meth)acrylic acid unit (a1) can be a methacrylic acid or acrylic acid unit, wherein an acrylic acid unit is preferable.

The at least one (meth)acrylic acid ester unit (a2) can be a methacrylic acid ester unit or an acrylic acid ester unit, wherein an acrylic acid ester unit, particularly acrylic acid (C1-4) acrylic ester unit is exemplary.

Exemplary structural units (a2) are acrylic acid methyl ester, methacrylic acid methyl ester, acrylic acid ethyl ester, methacrylic acid ethyl ester, acrylic acid propyl ester, methacrylic acid propyl ester, acrylic acid isopropyl ester, methacrylic acid isopropyl ester, acrylic acid butyl ester and methacrylic acid butyl ester.

Suitable anionic acrylate copolymers (a) are commercially available under the INCI designation Acrylates Copolymer. The anionic acrylate copolymer (a) Aculyn® 33A from Rohm & Haas is most preferred. In the commercially available form, this has a solids content of approximately 27.5 to 28.5 wt. % and a pH value of from about 2.1 to about 3.3.

An exemplary cosmetic composition for the temporary shaping of keratinous fibers contains:
(a) at least one crosslinked copolymer (a), which is composed of at least one of the following polymer units:
(a1) at least one acrylic acid unit,
(a2) at least one acrylic acid-(C1-4)-alkyl ester unit
and
(b) at least one crosslinked acrylate copolymer (b) differing from the copolymer (a), which includes at least one of the following structural units (b1) and (b2):

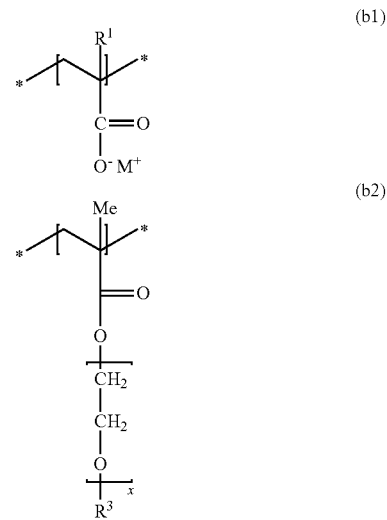

wherein
$R^1$ denotes a hydrogen atom or a methyl group,
$R^3$ denotes a $(C_8\text{-}C_{30})$-alkyl group,
$M^+$ denotes a physiologically tolerated cation and
x denotes an integer from about 5 to about 35.

This cosmetic composition claimed contained the crosslinked acrylate copolymer (b) in a quantity from about 0.1 to about 10 wt. %, such as from about 0.5 to about 7.0 wt. %, for example from about 0.7 to about 5.0 wt. % relative to the total weight of the cosmetic composition, specified as the solids content of active substance in the cosmetic composition.

The crosslinked anionic acrylate copolymer (b) includes at least the following structural units (b1) and (b2).

The crosslinked acrylate copolymer (b) is amphiphile based on the integral structural units.

A person skilled in the art understands "amphiphile" to generally mean that one and the same molecule comprises hydrophilic structural elements (e.g. of formula (b1)) and lipophilic structural elements (e.g. of formula b2)).

In the above formulae and all formulae below, a chemical bond bearing the symbol * denotes a free valence of the corresponding structural fragment. Ammonium ion and cationic organic compounds having a quaternized nitrogen atom are particularly suitable as physiologically compatible cations $M^+$ for compensation of the negative charge of the amphiphilic, anionic polymer metal cations of the physiologically compatible metals from the groups Ia, Ib, IIa, IIb, IIIb, Via or VIII of the period system of elements. Cationic organic compounds having a quaternized nitrogen atom are, for example, produced by employing protonation of primary, secondary or tertiary organic amines with an acid, or by employing permanent quaternization of said organic amines. Examples of such cationic organic ammonium compounds are 2-ammonioethanol and 2-trimethylammonioethanol.

The terms "crosslinked" and "crosslinking" in the context of the present disclosure are understood to mean the linking of polymer chains with each other by employing covalent chemical bonding with formation of a network. This covalent linking of polymer chains may take place by employing direct covalent bonding or by employing a molecular fragment bridging the polymer chain. The molecular fragment connects to the polymer chains bridged by the molecular fragment by employing covalent chemical bonding in each case.

The crosslinking of the crosslinked copolymers (b) can be for example produced using at least one crosslinked monomer. In the process, it is possible that the crosslinked monomers are selected from at least one compound of the group comprising polyunsaturated aromatic monomers (such as divinylbenzene, divinylnaphthalene, trivinylbenzene), polyunsaturated alicyclic monomers (such as 1,2,4-trivinylcyclohexane), di-functional esters of phthalic acid (such as diallyl phthalate), polyunsaturated aliphatic monomers (such as dienes, trienes, tetraenes such as isoprene, 1,3-butadiene, 1,5-hexadiene, 1,5,9-decatriene, 1,9-decadiene,
1,5-heptadiene), polyalkenyl ethers (such as triallyl pentaerythritol, diallyl pentaerythritol, diallyl sucrose, octaallyl sucrose, trimethylolpropane diallyl ether), polyunsaturated esters of polyalcohols or polyacids (such as 1,6-hexanediol di(meth)acrylate, tetramethylene tri(meth)acrylate, allyl acrylate, diallyl itaconate, diallyl fumarate, diallyl maleate, trimethylolpropane tri(meth)acrylate, trimethylolpropane di(meth)acrylate, polyethylene glycol di(meth)acrylate), alkylene bisacrylamides (such as methylene bisacrylamide, propylene bisacrylamide) hydroxy- and carboxy derivatives of methylene bisacrylamide (such as N,N'-bis-methylol methylene-bis-acrylamide), polyethylene glycol di(meth) acrylates (such as ethylene glycol di(meth)acrylate, diethyleneglycol di(meth)acrylate, triethylene glycoldi(meth) acrylate), polyunsaturated silanes (such as dimethylvinylsilane, methyltrivinylsilane, allyl dimethylvinylsilane, diallyl dimethylsilane, tetravinylsilane), n-methylolacrylamide; n-alkoxy(meth) acrylamide, wherein the alkoxy group is a (c1 to c18)-alkoxy group, unsaturated hydrolyzable silanes (such as triethoxyvinylsilane, tris-isopropoxy-vinylsilane, 3-triethoxysilyl-propylmethacrylate), hydrolyzable silanes (such as ethyltriethoxysilane, ethyltrimethoxysilane), epoxy-substituted hydrolyzable silanes (such as 2-(3,4-epoxycyclohexyl)ethyltriethoxysilane, 3-glycidoxypropyltrimethyoxysilane) polyisocyanates (such as 1,4-diisocyanatobutane, 1,6-diisocyanatohexane, 1,4-phenylenediamine diisocyanate, 4,4'-oxybis(phenylisocyanate), unsaturated epoxides (such as glycidylmethacrylates, allyl glycidyl ether), polyepoxides (such asdiglycidyl ether, 1,2,5,6-diepoxy hexane, ethylene glycol diglycidyl ether), ethoxylated polyols (such as diols, triols and diphenols, each ethoxylated with from about 2 to about 100 moles of ethylene oxide per mole of hydroxyl groups and terminated with a polymerizable unsaturated group, such as, vinyl ether, allyl ether, acrylate ester, methacrylate ester; examples comprise bisphenol A ethoxylated di(meth)acrylate, bisphenol F ethoxylated di(meth)acrylate, ethoxylated trimethylolpropane tri(meth)acrylates, acrylate and methacrylate esters of polyols having at least two acrylate ester or methacrylate ester-functionalities (such as trimethylolpropane triacrylate (TMPTA), trimethylolpropane ethoxylated (15) triacrylate (TMPEO15TA), trimethylolpropane dimethacrylate, triethyleneglycoldimethacrylate (TEGDMA), with about 30 mol of ethylene oxide ethoxylated bis-phenol A-dimethacrylate (EOBDMA)).

As contemplated herein, the copolymer (b) can be composed of additional structure units. In an exemplary embodiment, the copolymer (b) of at least about 30 wt. %, such as from about 40 to about 98 wt. % and for example at least from about 50 to about 95 wt. % of monomers (b1) and (b2). However, in an exemplary embodiment of the present disclosure, the copolymer (b) consists only of units (b1) and (b2) and units to be crosslinked, i.e. it is composed of these structural units.

The at least one unit (b1) is a (meth)acrylic acid unit and, as contemplated herein, can be a methacrylic acid unit and/or acrylic acid unit. For example, the unit (b1) is a methacrylic acid unit ($R^1$ in formula (b1) denotes a methyl group). Corresponding acrylic polymers (b) have been found to be useful for cosmetic applications.

In one embodiment, x in the structural unit (b2) of the crosslinked acrylate copolymer (b) denotes an integer from about 10 to about 24, such as from about 16 to about 22, for example about 20.

In one embodiment, $R^3$ in unit (b2) of the crosslinked acrylate copolymer (b) denotes a ($C_{12}$-$C_{20}$)-alkyl group, such as a ($C_{14}$-$C_{20}$)-alkyl group, also for example a ($C_{16}$-$C_{18}$)-alkyl group. The alkyl group in this context is possibly linear, but can also be branched. $R^3$ denotes, in particular, a combination of linear $C_{16}$- and $C_{18}$-alkyl groups, i.e. stearyl- and cetyl groups (INCI: ceteareth). Corresponding acrylic polymers (b) have been found to be useful for cosmetic applications.

In one embodiment, the contained crosslinked acrylate copolymer (b) is a crosslinked acrylate copolymer with the INCI designation Acrylates-Ceteareth-20 Methacrylate Crosspolymer. In some embodiments, the crosslinked acrylate copolymer (b) is a crosslinked acrylate copolymer available under the trade name BALANCE® RCF (AkzoNobel). The latter is an approximately 30 wt. % dispersion in water.

Additional crosslinked acrylate copolymers (b) are identified by the INCI designation Acrylates/Steareth-20 Methacrylate Crosspolymer. In such crosslinked acrylate copolymers, the at least one unit (a1) is a (meth)acrylic acid unit and, as contemplated herein, can be a methacrylic acid unit and/or acrylic acid unit. They have about 20 units of ethylene oxide and are etherified with stearyl alcohol. One such polymer, for example, is available under the trade name Aculyn® 88 (Rohm & Haas). In the commercially available form, this has a solids content of approximately 28 to 33 wt. % and a pH value of from about 3.3 to about 4.3.

Compared to alternative cosmetic agents, the cosmetic compositions as contemplated herein are exemplified by an improved long-term hold, in addition to the aforementioned advantages. A weight ratio of polymers a) and b) in the cosmetic composition of from about 5:1 to about 1:5, such as from about 3:1 to about 1:3 and for example from about 2:1 to about 1:2 has been found to be useful for the cosmetic properties of the inventive agent.

In an embodiment of the present disclosure, the cosmetic composition contains the copolymer commercially available under the name Aculyn® 33A as the copolymer (a) and the copolymer commercially available under the name BAL- ANCE® RCF as the crosslinked acrylate copolymer (b). Good results with regard to a combination of stiffness and long-term hold were achieved with this combination. This polymer combination is useful for styling products in gel form.

Additional properties generally useful in styling products, such as moisture resistance and low stickiness, are also provided with this combination, for example when packaged as hair gel.

Copolymers (a) and (b) are used in the cosmetic composition in a partially neutralized or neutralized form. At least one alkanolamine is preferably used for neutralization. The alkanolamines used as an alkalization agent in the context of the present disclosure are selected from primary amines with a $C_2$-$C_6$-alkyl base body having at least one hydroxyl group. It is possible that alkanolamines are selected from the group comprising 2-aminoethan-1-ol (monoethanolamine), 3-(2-hydroxyethyl)-amine (triethanolamine), 3-aminopropan-1-ol, 4-amino-butan-1-ol, 5-aminopentan-1-ol, 1-aminopropan-2-ol, 1-aminobutan-2-ol, 1-aminopentan-2-ol, 1-aminopentan-3-ol, 1-aminopentan-4-ol, 3-amino-2-methylpropan-1-ol, 1-amino-2-methylpropan-2-ol, 3-aminopropan-1,2-diol, 2-amino-2-methylpropan-1,3-diol. As contemplated herein, it is also possible that alkanolamines are selected from the group of 2-aminoethan-1-ol, 2-amino-2-methylpropan-1-ol and 2-amino-2-methyl-propan-1,3-diol. In this context, 2-amino-2-methylpropanol has been found to be particularly suitable as a neutralization agent. Therefore, agents as contemplated herein contain 2-amino-2-methylpropanol. The 2-amino-2-methylpropanol is used in the inventive agents in a quantity which does not exceed the quantity required for neutralization of copolymers (a) and (b). The quantities of 2-amino-2-methylpropanol used in the composition claimed are from about 80 to about 100%, such as from about 90 to about 100% and for example from about 95 to about 100% of the quantity required for complete neutralization of copolymers (a) and (B). In an embodiment, the proportion by weight of the 2-amino-2-methylpropanol to the total weight of the cosmetic agent is from about 0.05 to about 7.0 wt. %, such as from about 0.1 to about 5.0 wt. % and for example from about 0.1 to about 3.0 wt. %.

In summary, a cosmetic composition for the temporary shaping of keratinous fibers contains, relative to its total weight:

(a) from about 0.7 to about 5.0 wt. % of at least one acrylate copolymer (a) including of at least the following monomer units:

(a1) at least one acrylic acid unit, (a2) at least one acrylic acid-(C1-4)-alkyl ester unit and (b) from about 0.7 to about 5.0 wt. % of at least one crosslinked acrylate copolymer (b) differing from the copolymer (a), which of at least one of the following structural units (b1) and (b2):

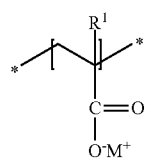

(b1)

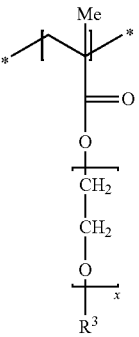

(b2)

wherein
$R^1$ denotes a methyl group,
$R^3$ denotes a $(C_{14}$-$C_{20})$-alkyl group,
$M^+$ denotes a physiologically tolerated cation and
x denotes an integer from about 16 to about 22.

The cosmetic composition according to the present disclosure contains one or more additional component(s) which differ(s) from the copolymers (a) and (b) and aid the thickening agent or the gel formation or film formation. Examples are cationic, anionic, nonionic or amphoteric polymers. The proportion by weight of these additional components to the total weight of the cosmetic composition can be comparatively low due to the present of components (a) and (B) and, for example, be from about 0.02 to about 3 wt. %, such as from about 0.05 to about 1.5 wt. % and for example from about 0.2 to about 0.8 wt. %.

Examples are acrylamide/ammonium acrylate copolymer, acrylamides/DMAPA acrylates/methoxy PEG methacrylate copolymer, acrylamidopropyltrimonium chloride/acrylamide copolymer, acrylamidopropyltrimonium chloride/Acrylates Copolymer, acrylates/acetoacetoxyethyl methacrylate copolymer, acrylates/acrylamide copolymer, acrylates/ammonium methacrylate copolymer, acrylates/t-butylacrylamide copolymer, acrylates/C1-2 succinates/hydroxyAcrylates Copolymer, acrylates/lauryl acrylate/stearyl acrylate/ethylamine oxide methacrylate copolymer, acrylates/octylacrylamide copolymer, acrylates/octylacrylamide/diphenyl amodimethicone copolymer, acrylates/stearyl acrylate/ethylamine oxide methacrylate copolymer, acrylates/CA copolymer, acrylates/vp copolymer, adipic acid/diethylenetriamine copolymer, adipic acid/dimethylaminohydroxypropyl diethylenetriamine copolymer, adipic acid/epoxypropyl diethylenetriamine copolymer, adipic acid/isophthalic acid/neopentyl glycol/trimethylolpropane copolymer, allyl stearate/VA copolymer, aminoethylacrylate phosphate/Acrylates Copolymer, aminoethylpropanediol-acrylates/acrylamide copolymer, aminoethylpropanediol-AMPD-acrylates/diacetoneacrylamide copolymer, ammonium va/Acrylates Copolymer, AMPD-acrylates/diacetoneacrylamide copolymer, AMP-acrylates/allyl methacrylate copolymer, AMP-acrylates/$C_{1-18}$ alkyl acrylates/$C_{1-8}$ alkyl acrylamide copolymer, AMP-acrylates/diacetoneacrylamide copolymer, AMP-acrylates/dimethylaminoethylmethacrylate copolymer, bacillus/rice bran extract/soybean extract ferment filtrate, bis-butyloxyamodimethicone/PEG-60 copolymer, butyl acrylate/ethylhexyl methacrylate copolymer, butyl acrylate/hydroxypropyl dimethicone acrylate copolymer, butylated PVP, butyl ester of ethylene/MA copolymer, butyl ester of PVM/MA copolymer, calcium/sodium PVM/MA copolymer, corn starch/acrylamide/sodium acrylate copolymer, diethylene glycolamine/epichlorohydrin/piperazine copolymer, dimethicone crosspolymer, diphenyl amodimethicone, ethyl ester of PVM/MA copolymer, hydrolyzed wheat protein/PVP crosspolymer, isobutylene/ethylmaleimide/hydroxyethylmaleimide copolymer, isobutylene/MA copolymer, isobutylmethacrylate/bis-hydroxypropyl dimethicone acrylate copolymer, isopropyl ester of PVM/MA copolymer, lauryl acrylate crosspolymer, lauryl methacrylate/glycol dimethacrylate crosspolymer, MEA-sulfite, methacrylic acid/sodium acrylamidomethyl propane sulfonate copolymer, methacryloyl ethyl betaine/Acrylates Copolymer, octylacrylamide/acrylates/butylaminoethyl methacrylate copolymer, PEG/PPG-25/25 dimethicone/Acrylates Copolymer, PEG-8/SMDI copolymer, polyacrylamide, polyacrylate-6, polybeta-alanine/glutaric acid crosspolymer, polybutylene terephthalate, polyester-1, polyethylacrylate, polyethylene terephthalate, polymethacryloyl ethyl betaine, polypentaerythrityl terephthalate, polyperfluoroperhydrophenanthrene, polyquaternium-1, polyquaternium-2, polyquaternium-4, polyquaternium-5, polyquaternium-6, polyquaternium-7, polyquaternium-8, polyquaternium-9, polyquaternium-10, polyquaternium-11, polyquaternium-12, polyquaternium-13, polyquaternium-14, polyquaternium-15, polyquaternium-16, polyquaternium-17, polyquaternium-18, polyquaternium-19, polyquaternium-20, polyquaternium-22, polyquaternium-24, polyquaternium-27, polyquaternium-28, polyquaternium-29, polyquaternium-30, polyquaternium-31, polyquaternium-32, polyquaternium-33, polyquaternium-34, polyquaternium-35, polyquaternium-36, polyquaternium-37, polyquaternium-39, polyquaternium-45, polyquaternium-46, polyquaternium-47, polyquaternium-48, polyquaternium-49, polyquaternium-50, polyquaternium-55, polyquaternium-56, polysilicone-9, polyurethane-1, polyurethane-6, polyurethane-10, polyvinyl acetate, polyvinyl butyral, polyvinylcaprolactam, polyvinylformamide, polyvinyl imidazolinium acetate, polyvinyl methyl ether, potassium butyl ester of pvm/ma copolymer, potassium ethyl ester of PVM/MA copolymer, PPG-70 polyglyceryl-10 ether, PPG-12/SMDI copolymer, ppg-51/SMDI copolymer, PPG-10 sorbitol, PVM/MA copolymer, PVP, PVP/VA/itaconic acid copolymer, PVP/VA/vinyl propionate copolymer, rhizobian gum, rosin acrylate, shellac, sodium butyl ester of PVM/MA copolymer, sodium ethyl ester of PVM/MA copolymer, sodium polyacrylate, *sterculia urens* gum, terephthalic acid/isophthalic acid/sodium isophthalic acid sulfonate/glycol copolymer, trimethylolpropane triacrylate, trimethylsiloxysilylcarbamoyl pullulan, VA/crotonates copolymer, VA/crotonates/methacryloxybenzophenone-1 copolymer, VA/crotonates/vinyl neodecanoate copolymer, VA/crotonates/vinyl propionate copolymer, VA/DBM copolymer, VA/vinyl butyl benzoate/crotonates copolymer, vinylamine/vinyl alcohol copolymer, vinyl caprolactam/VP/dimethylaminoethyl methacrylate copolymer, VP/acrylates/lauryl methacrylate copolymer, VP/dimethylaminoethylmethacrylate copolymer, VP/DMAPA Acrylates Copolymer, VP/hexadecene copolymer, VP/VA copolymer, VP/vinyl caprolactam/DMAPA Acrylates Copolymer, yeast palmitate and styrene/VP copolymer.

The further component acting as a gelling agent may be a homopolyacrylic acid (INCI: Carbomer), which is available commercially under the name Carbopol® in various forms. The carbomer is contained in a proportion of from about 0.02 to about 3 wt. %, such as from about 0.05 to about 1.5 wt. % and for example from about 0.2 to about 0.8 wt. %, relative to the total weight of the cosmetic composition.

To further improve the cosmetic effect, some compositions contain, in addition to the crosslinked copolymers (a) and (b) and an optionally added thickening agent or gel former, a film-forming polymer (c) differing from these ingredients, for example an anionic or nonionic polymer (c).

Examples of nonionic polymers are:

vinylpyrrolidone/vinylester copolymers, which are sold, for example, under the trade name Luviskol (BASF). Luviskol VA 64 and Luviskol VA 73, in each case vinylpyrrolidone/vinylacetate-copolymers, may be nonionic polymers.

cellulose ethers, such as hydroxypropyl cellulose, hydroxyethyl cellulose and methylhydroxypropyl cellulose, are sold, for example, under the trade name Culminaland Benecel (AQUALON).

shellac.

vinylpyrrolidones, which are sold, for example, under the name Luviskol (BASF).

siloxanes. These siloxanes can be water-soluble or non-water-soluble. Volatile and non-volatile siloxanes are suitable, wherein non-volatile siloxanes are to be understood to mean such compounds having a boiling point above about 200° C. under normal pressure. Exemplary siloxanes are polydialkylsiloxanes, such as polydimethylsiloxane, polyalkylarylsiloxanes, such as polyphenylmethylsiloxane, ethoxylated polydialkylsiloxanes and polydialkylsiloxanes which contain amine and/or hydroxyl groups.

glycosidically substituted silicones.

The film-forming polymers used as contemplated herein because of their cosmetic effect in combination with copolymers a) and b) are the polyvinylpyrrolidones (INCI designation: PVP) and the vinyl-pyrrolidone/vinyl-acetate copolymers (INCI designation VP/VA copolymer). The proportion by weight of these polymers may be limited to quantities between about 1.0 and about 10 wt. %. Exemplary cosmetic compositions as contemplated herein, therefore, are exemplified in that they contain an additional from about 1.0 to about 10 wt. % of polyvinylpyrrolidone and/or vinylpyrrolidone/vinylacetate-copolymer, such as polyvinylpyrrolidone, relative to their total weight. Exemplary cosmetic agents have a proportion by weight of from about 2.0 to about 8.5 wt. %, such as from about 3.0 to about 7.0 wt. % of polyvinylpyrrolidone and/or vinylpyrrolidone/vinylacetate-copolymers c), relative to the total weight of the cosmetic agent.

The cosmetic composition claimed can contain additional conventional ingredients of styling products. Additional care substances, in particular, can be mentioned as additional suitable auxiliary substances and additives.

As the nourishing agent, the agent can contain at least one protein hydrolysate and/or a derivate thereof, for example. Protein hydrolysates are product mixtures obtained through the acidically, basically or enzymatically catalyzed decomposition of proteins. As contemplated herein, the expression protein hydrolysates also includes total hydrolysates, as well as individual amino acids and the derivatives thereof, as well as mixtures of various amino acids. The molecular weight of the protein hydrolysates usable as contemplated herein is between about 75, the molecular weight for glycine, and about 200,000, such as from about 75 to about 50,000 and most for example from about 75 to about 20,000 Daltons.

The agent as contemplated herein can also contain, as a nourishing agent a vitamin, a provitamin, a vitamin precursor and/or a derivative thereof. As contemplated herein, such vitamins, provitamins and vitamin precursors are usually assigned to the groups A, B, C, E, F and H.

Similar to the addition of glycerine and/or propylene glycol, the addition of panthenol increases the flexibility of the polymer film formed using the inventive agent. The agent as contemplated herein can also contain, as a nourishing agent, a plant extract, as well as mono- and/or oligosaccharides and/or lipids.

Furthermore, oil bodies are suitable as care substances. The natural and synthetic cosmetic oil bodies include, for example, vegetable oils, liquid paraffin oils, isoparaffin oils and synthetic hydrocarbons, and di-n-alkyl ethers having a total of between about 12 to about 36 carbon atoms, in particular between about 12 to about 24 carbon atoms. Cosmetic agents as contemplated herein contain at least one oil body, such as at least one oil body from the group of silicone oils. The group of silicone oils also includes, for example, dimethicones, which also include cyclomethicones, amino-functional silicones and dimethiconols. Dimethicones can be linear or branched, as well as cyclical or cyclical and branched. Suitable silicone oils or silicone gums are, in particular dialkyl- and alkylarylsiloxanes, such as dimethylpolysiloxane and methylphenylpolysiloxane, and alkoxylated, quaternized or anionic derivatives thereof. Cyclical and linear polydialkylsiloxanes, alkoxylated and/or aminated derivatives thereof, dihydroxypolydimethylsiloxanes and polyphenylalkylsiloxanes are exemplary. Ester oils, i.e. esters of 6-$C_{30}$ fatty acids with $C_2$-$C_{30}$ fatty alcohols, such as monoesters of fatty acids with alcohols having from about 2 to about 24 carbon atoms, such as isopropyl myristate (Rilanit® IPM), isononanoic acid $C_{16-18}$ alkyl esters (Cetiol® SN), 2-ethylhexyl palmitate (Cegesoft®24), stearic acid 2-ethylhexyl ester (Cetiol® 868), cetyl oleate, glycerol tricaprylate, coconut fatty alcohol caprinate/caprylate (Cetiol® LC), n-butyl stearate, oleyl erucate (Cetiol® J 600), isopropyl palmitate (Rilanit® IPP), oleyl oleate (Cetiol®), lauric acid hexyl ester (Cetiol® A), di-n-butyl adipate (Cetiol® B), myristyl myristate (Cetiol® MM), cetearyl isononanoate (Cetiol® SN), oleic acid decyl ester (Cetiol® V) are additional care oil bodies.

Furthermore, dicarboxylic acid esters, symmetrical, asymmetrical or cyclic esters of carbonic acid with fatty alcohols, trifatty acid esters of saturated and/or unsaturated linear and/or branched fatty acids with glycerol or fatty acid partial glycerides, which are to be understood as monoglycerides, diglycerides and technical mixtures thereof are suitable as care substances.

Furthermore, emulsifiers and/or surfactants may be contained in the composition claimed. PEG derivatives of hydrated castor oil are preferred, which are available, for example, under the name PEG Hydrogenated Castor Oil, such as PEG-30 Hydrogenated Castor Oil, PEG-33 Hydrogenated Castor Oil, PEG-35 Hydrogenated Castor Oil, PEG-36 Hydrogenated Castor Oil or PEG-40 Hydrogenated Castor Oil. As contemplated herein, use of PEG-40 Hydrogenated Castor Oil is possible. These are contained in a quantity of from about 0.05 to about 1.5 wt. %, such as from about 0.1 to about 1.0 wt. %, also for example from about 0.2 to about 0.8 wt. % or from about 0.3 to about 0.6 wt. %.

The cosmetic agents claimed contain the ingredients and/or active ingredients in a cosmetically acceptable carrier.

Cosmetically acceptable carriers are aqueous, alcoholic or aqueous-alcoholic media having at least about 10 wt. % water, relative to the total weight of the agent. It is possible that the inventive cosmetic carrier contains water, for example in a quantity that is preferably at least about 10 wt. %, such as at least about 20.0 wt %, possibly at least about 40 wt. % water relative to the total weight of the agent. Cosmetic agents may have a proportion of water between about 50 and about 95 wt. %, such as between about 60 and about 90 wt. % and for example between about 65 and about 85 wt. %, relative to their total weight.

Low alcohols having from about 1 to about 4 carbon atoms conventionally used for cosmetic purpose, such as ethanol and isopropanol, can be used, in particular as alcohols. Examples of water-soluble solvents as a cosolvent are glycerol and/or ethylene glycol and/or 1,2-propylene glycol in a quantity of from about 0 to about 30 wt. % relative to the total agent.

Tabular Overview

A summary of some cosmetic agents is provided in the following tables (specifications in wt. % relative to the total weight of the cosmetic agent, unless otherwise specified).

|  | Formula 1 | Formula 2 | Formula 3 | Formula 4 | Formula 5 |
| --- | --- | --- | --- | --- | --- |
| Copolymer a) | 0.1 to 10 | 0.2 to 8.0 | 0.5 to 7.0 | 0.6 to 4.0 | 0.7 to 5.0 |
| Copolymer b) | 0.1 to 10 | 0.2 to 8.0 | 0.5 to 7.0 | 0.6 to 4.0 | 0.7 to 5.0 |
| Misc | add 100 | add 100 | add 100 | add 100 | add 100 |

|  | Formula 1a | Formula 2a | Formula 3a | Formula 4a | Formula 5a |
| --- | --- | --- | --- | --- | --- |
| Acrylates Copolymer | 0.1 to 10 | 0.2 to 8.0 | 0.5 to 7.0 | 0.6 to 4.0 | 0.7 to 5.0 |
| Acrylates/Ceteareth-20 Methacrylate Crosspolymer | 0.1 to 10 | 0.2 to 8.0 | 0.5 to 7.0 | 0.6 to 4.0 | 0.7 to 5.0 |
| Misc | add 100 | add 100 | add 100 | add 100 | add 100 |

|  | Formula 1b | Formula 2b | Formula 3b | Formula 4b | Formula 5b |
| --- | --- | --- | --- | --- | --- |
| Aculyn® 33A (specifications as solids content) | 0.1 to 10 | 0.2 to 8.0 | 0.5 to 7.0 | 0.6 to 4.0 | 0.7 to 5.0 |
| BALANCE® RCF (specifications as solids content) | 0.1 to 10 | 0.2 to 8.0 | 0.5 to 7.0 | 0.6 to 4.0 | 0.7 to 5.0 |
| Misc | add 100 | add 100 | add 100 | add 100 | add 100 |

|  | Formula 6 | Formula 7 | Formula 8 | Formula 9 | Formula 10 |
| --- | --- | --- | --- | --- | --- |
| Copolymer a) | 0.1 to 10 | 0.2 to 8.0 | 0.5 to 7.0 | 0.6 to 4.0 | 0.7 to 5.0 |
| Copolymer b) | 0.1 to 10 | 0.2 to 8.0 | 0.5 to 7.0 | 0.6 to 4.0 | 0.7 to 5.0 |
| Polyvinylpyrrolidone | 1.0 to 10 | 2.0 to 8.5 | 2.0 to 8.5 | 3.0 to 7.0 | 3.0 to 7.0 |

-continued

| | | | | | |
|---|---|---|---|---|---|
| Misc | add 100 | add 100 | add 100 | add 100 | add 100 |

| | Formula 6a | Formula 7a | Formula 8a | Formula 9a | Formula 10a |
|---|---|---|---|---|---|
| Acrylates Copolymer | 0.1 to 10 | 0.2 to 8.0 | 0.5 to 7.0 | 0.6 to 4.0 | 0.7 to 5.0 |
| Acrylates/Ceteareth-20 Methacrylate Crosspolymer | 0.1 to 10 | 0.2 to 8.0 | 0.5 to 7.0 | 0.6 to 4.0 | 0.7 to 5.0 |
| Polyvinylpyrrolidone | 1.0 to 10 | 2.0 to 8.5 | 2.0 to 8.5 | 3.0 to 7.0 | 3.0 to 7.0 |
| Misc | add 100 | add 100 | add 100 | add 100 | add 100 |

| | Formula 6b | Formula 7b | Formula 8b | Formula 9b | Formula 10b |
|---|---|---|---|---|---|
| Aculyn ® 33A (specifications as solids content) | 0.1 to 10 | 0.2 to 8.0 | 0.5 to 7.0 | 0.6 to 4.0 | 0.7 to 5.0 |
| BALANCE ® RCF (specifications as solids content) | 0.1 to 10 | 0.2 to 8.0 | 0.5 to 7.0 | 0.6 to 4.0 | 0.7 to 5.0 |
| Polyvinylpyrrolidone | 1.0 to 10 | 2.0 to 8.5 | 2.0 to 8.5 | 3.0 to 7.0 | 3.0 to 7.0 |
| Misc | add 100 | add 100 | add 100 | add 100 | add 100 |

| | Formula 11 | Formula 12 | Formula 13 | Formula 14 | Formula 15 |
|---|---|---|---|---|---|
| Copolymer a) | 0.1 to 10 | 0.2 to 8.0 | 0.5 to 7.0 | 0.6 to 4.0 | 0.7 to 5.0 |
| Copolymer b) | 0.1 to 10 | 0.2 to 8.0 | 0.5 to 7.0 | 0.6 to 4.0 | 0.7 to 5.0 |
| Vinylpyrrolidone/Vinylacetate-Copolymer | 1.0 to 10 | 2.0 to 8.5 | 2.0 to 8.5 | 3.0 to 7.0 | 3.0 to 7.0 |
| Misc | add 100 | add 100 | add 100 | add 100 | add 100 |

| | Formula 11a | Formula 12a | Formula 13a | Formula 14a | Formula 15a |
|---|---|---|---|---|---|
| Acrylates Copolymer | 0.1 to 10 | 0.2 to 8.0 | 0.5 to 7.0 | 0.6 to 4.0 | 0.7 to 5.0 |
| Acrylates/Ceteareth-20 Methacrylate Crosspolymer | 0.1 to 10 | 0.2 to 8.0 | 0.5 to 7.0 | 0.6 to 4.0 | 0.7 to 5.0 |
| Vinylpyrrolidone/Vinylacetate-Copolymer | 1.0 to 10 | 2.0 to 8.5 | 2.0 to 8.5 | 3.0 to 7.0 | 3.0 to 7.0 |
| Misc | add 100 | add 100 | add 100 | add 100 | add 100 |

| | Formula 11b | Formula 12b | Formula 13b | Formula 14b | Formula 15b |
|---|---|---|---|---|---|
| Aculyn ® 33A (specifications as solids content) | 0.1 to 10 | 0.2 to 8.0 | 0.5 to 7.0 | 0.6 to 4.0 | 0.7 to 5.0 |
| BALANCE ® RCF (specifications as solids content) | 0.1 to 10 | 0.2 to 8.0 | 0.5 to 7.0 | 0.6 to 4.0 | 0.7 to 5.0 |
| Vinylpyrrolidone/Vinylacetate-Copolymer | 1.0 to 10 | 2.0 to 8.5 | 2.0 to 8.5 | 3.0 to 7.0 | 3.0 to 7.0 |
| Misc | add 100 | add 100 | add 100 | add 100 | add 100 |

| | Formula 16 | Formula 17 | Formula 18 | Formula 19 | Formula 20 |
|---|---|---|---|---|---|
| Copolymer a) | 0.1 to 10 | 0.2 to 8.0 | 0.5 to 7.0 | 0.6 to 4.0 | 0.7 to 5.0 |
| Copolymer b) | 0.1 to 10 | 0.2 to 8.0 | 0.5 to 7.0 | 0.6 to 4.0 | 0.7 to 5.0 |
| Carbomer | 0.02 to 3.0 | 0.05 to 2.0 | 0.05 to 1.5 | 0.2 to 1.0 | 0.4 to 0.8 |
| Misc | add 100 | add 100 | add 100 | add 100 | add 100 |

| | Formula 16a | Formula 17a | Formula 18a | Formula 19a | Formula 20a |
|---|---|---|---|---|---|
| Acrylates Copolymer | 0.1 to 10 | 0.2 to 8.0 | 0.5 to 7.0 | 0.6 to 4.0 | 0.7 to 5.0 |
| Acrylates/Ceteareth-20 Methacrylate Crosspolymer | 0.1 to 10 | 0.2 to 8.0 | 0.5 to 7.0 | 0.6 to 4.0 | 0.7 to 5.0 |
| Carbomer | 0.02 to 3.0 | 0.05 to 2.0 | 0.05 to 1.5 | 0.2 to 1.0 | 0.4 to 0.8 |
| Misc | add 100 | add 100 | add 100 | add 100 | add 100 |

| | Formula 16b | Formula 17b | Formula 18b | Formula 19b | Formula 20b |
|---|---|---|---|---|---|
| Aculyn ® 33A (specifications as solids content) | 0.1 to 10 | 0.2 to 8.0 | 0.5 to 7.0 | 0.6 to 4.0 | 0.7 to 5.0 |
| BALANCE ® RCF (specifications as solids content) | 0.1 to 10 | 0.2 to 8.0 | 0.5 to 7.0 | 0.6 to 4.0 | 0.7 to 5.0 |

-continued

| | | | | | |
|---|---|---|---|---|---|
| Carbomer | 0.02 to 3.0 | 0.05 to 2.0 | 0.05 to 1.5 | 0.2 to 1.0 | 0.4 to 0.8 |
| Misc | add 100 | add 100 | add 100 | add 100 | add 100 |

| | Formula 21 | Formula 22 | Formula 23 | Formula 24 | Formula 25 |
|---|---|---|---|---|---|
| Copolymer a) | 0.1 to 10 | 0.2 to 8.0 | 0.5 to 7.0 | 0.6 to 4.0 | 0.7 to 5.0 |
| Copolymer b) | 0.1 to 10 | 0.2 to 8.0 | 0.5 to 7.0 | 0.6 to 4.0 | 0.7 to 5.0 |
| PEG-40 Hydrogenated Castor Oil | 0.05 to 1.5 | 0.1 to 1.0 | 0.2 to 0.9 | 0.3 to 0.8 | 0.4 to 0.6 |
| Misc | add 100 | add 100 | add 100 | add 100 | add 100 |

| | Formula 21a | Formula 22a | Formula 23a | Formula 24a | Formula 25a |
|---|---|---|---|---|---|
| Acrylates Copolymer | 0.1 to 10 | 0.2 to 8.0 | 0.5 to 7.0 | 0.6 to 4.0 | 0.7 to 5.0 |
| Acrylates/Ceteareth-20 Methacrylate Crosspolymer | 0.1 to 10 | 0.2 to 8.0 | 0.5 to 7.0 | 0.6 to 4.0 | 0.7 to 5.0 |
| PEG-40 Hydrogenated Castor Oil | 0.05 to 1.5 | 0.1 to 1.0 | 0.2 to 0.9 | 0.3 to 0.8 | 0.4 to 0.6 |
| Misc | add 100 | add 100 | add 100 | add 100 | add 100 |

| | Formula 21b | Formula 22b | Formula 23b | Formula 24b | Formula 25b |
|---|---|---|---|---|---|
| Aculyn ® 33A (specifications as solids content) | 0.1 to 10 | 0.2 to 8.0 | 0.5 to 7.0 | 0.6 to 4.0 | 0.7 to 5.0 |
| BALANCE ® RCF (specifications as solids content) | 0.1 to 10 | 0.2 to 8.0 | 0.5 to 7.0 | 0.6 to 4.0 | 0.7 to 5.0 |
| PEG-40 Hydrogenated Castor Oil | 0.05 to 1.5 | 0.1 to 1.0 | 0.2 to 0.9 | 0.3 to 0.8 | 0.4 to 0.6 |
| Misc | add 100 | add 100 | add 100 | add 100 | add 100 |

| | Formula 26 | Formula 27 | Formula 28 | Formula 29 | Formula 30 |
|---|---|---|---|---|---|
| Copolymer a) | 0.1 to 10 | 0.2 to 8.0 | 0.5 to 7.0 | 0.6 to 4.0 | 0.7 to 5.0 |
| Copolymer b) | 0.1 to 10 | 0.2 to 8.0 | 0.5 to 7.0 | 0.6 to 4.0 | 0.7 to 5.0 |
| Water | 50 to 95 | 50 to 95 | 60 to 90 | 60 to 90 | 65 to 85 |
| Misc | add 100 | add 100 | add 100 | add 100 | add 100 |

| | Formula 26a | Formula 27a | Formula 28a | Formula 29a | Formula 30a |
|---|---|---|---|---|---|
| Acrylates Copolymer | 0.1 to 10 | 0.2 to 8.0 | 0.5 to 7.0 | 0.6 to 4.0 | 0.7 to 5.0 |
| Acrylates/Ceteareth-20 Methacrylate Crosspolymer | 0.1 to 10 | 0.2 to 8.0 | 0.5 to 7.0 | 0.6 to 4.0 | 0.7 to 5.0 |
| Water | 50 to 95 | 50 to 95 | 60 to 90 | 60 to 90 | 65 to 85 |
| Misc | add 100 | add 100 | add 100 | add 100 | add 100 |

| | Formula 26b | Formula 27b | Formula 28b | Formula 29b | Formula 30b |
|---|---|---|---|---|---|
| Aculyn ® 33A (specifications as solids content) | 0.1 to 10 | 0.2 to 8.0 | 0.5 to 7.0 | 0.6 to 4.0 | 0.7 to 5.0 |
| BALANCE ® RCF (specifications as solids content) | 0.1 to 10 | 0.2 to 8.0 | 0.5 to 7.0 | 0.6 to 4.0 | 0.7 to 5.0 |
| Water | 50 to 95 | 50 to 95 | 60 to 90 | 60 to 90 | 65 to 85 |
| Misc | add 100 | add 100 | add 100 | add 100 | add 100 |

| | Formula 31 | Formula 32 | Formula 33 | Formula 34 | Formula 35 |
|---|---|---|---|---|---|
| Copolymer a) | 0.1 to 10 | 0.2 to 8.0 | 0.5 to 7.0 | 0.6 to 4.0 | 0.7 to 5.0 |
| Copolymer b) | 0.1 to 10 | 0.2 to 8.0 | 0.5 to 7.0 | 0.6 to 4.0 | 0.7 to 5.0 |
| Polyvinylpyrrolidone | 1.0 to 10 | 2.0 to 8.5 | 2.0 to 8.5 | 3.0 to 7.0 | 3.0 to 7.0 |
| Water | 50 to 95 | 50 to 95 | 60 to 90 | 60 to 90 | 65 to 85 |
| Misc | add 100 | add 100 | add 100 | add 100 | add 100 |

| | Formula 31a | Formula 32a | Formula 33a | Formula 34a | Formula 35a |
|---|---|---|---|---|---|
| Acrylates Copolymer | 0.1 to 10 | 0.2 to 8.0 | 0.5 to 7.0 | 0.6 to 4.0 | 0.7 to 5.0 |
| Acrylates/Ceteareth-20 Methacrylate Crosspolymer | 0.1 to 10 | 0.2 to 8.0 | 0.5 to 7.0 | 0.6 to 4.0 | 0.7 to 5.0 |
| Polyvinylpyrrolidone | 1.0 to 10 | 2.0 to 8.5 | 2.0 to 8.5 | 3.0 to 7.0 | 3.0 to 7.0 |
| Water | 50 to 95 | 50 to 95 | 60 to 90 | 60 to 90 | 65 to 85 |
| Misc | add 100 | add 100 | add 100 | add 100 | add 100 |

-continued

|  | Formula 31b | Formula 32b | Formula 33b | Formula 34b | Formula 35b |
|---|---|---|---|---|---|
| Aculyn ® 33A (specifications as solids content) | 0.1 to 10 | 0.2 to 8.0 | 0.5 to 7.0 | 0.6 to 4.0 | 0.7 to 5.0 |
| BALANCE ® RCF (specifications as solids content) | 0.1 to 10 | 0.2 to 8.0 | 0.5 to 7.0 | 0.6 to 4.0 | 0.7 to 5.0 |
| Polyvinylpyrrolidone | 1.0 to 10 | 2.0 to 8.5 | 2.0 to 8.5 | 3.0 to 7.0 | 3.0 to 7.0 |
| Water | 50 to 95 | 50 to 95 | 60 to 90 | 60 to 90 | 65 to 85 |
| Misc | add 100 | add 100 | add 100 | add 100 | add 100 |

|  | Formula 36 | Formula 37 | Formula 38 | Formula 39 | Formula 40 |
|---|---|---|---|---|---|
| Copolymer a) | 0.1 to 10 | 0.2 to 8.0 | 0.5 to 7.0 | 0.6 to 4.0 | 0.7 to 5.0 |
| Copolymer b) | 0.1 to 10 | 0.2 to 8.0 | 0.5 to 7.0 | 0.6 to 4.0 | 0.7 to 5.0 |
| Vinylpyrrolidone/ Vinylacetate-Copolymer | 1.0 to 10 | 2.0 to 8.5 | 2.0 to 8.5 | 3.0 to 7.0 | 3.0 to 7.0 |
| Water | 50 to 95 | 50 to 95 | 60 to 90 | 60 to 90 | 65 to 85 |
| Misc | add 100 | add 100 | add 100 | add 100 | add 100 |

|  | Formula 36a | Formula 37a | Formula 38a | Formula 39a | Formula 40a |
|---|---|---|---|---|---|
| Acrylates Copolymer | 0.1 to 10 | 0.2 to 8.0 | 0.5 to 7.0 | 0.6 to 4.0 | 0.7 to 5.0 |
| Acrylates/Ceteareth-20 Methacrylate Crosspolymer | 0.1 to 10 | 0.2 to 8.0 | 0.5 to 7.0 | 0.6 to 4.0 | 0.7 to 5.0 |
| Vinylpyrrolidone/ Vinylacetate-Copolymer | 1.0 to 10 | 2.0 to 8.5 | 2.0 to 8.5 | 3.0 to 7.0 | 3.0 to 7.0 |
| Water | 50 to 95 | 50 to 95 | 60 to 90 | 60 to 90 | 65 to 85 |
| Misc | add 100 | add 100 | add 100 | add 100 | add 100 |

|  | Formula 36b | Formula 37b | Formula 38b | Formula 39b | Formula 40b |
|---|---|---|---|---|---|
| Aculyn ® 33A (specifications as solids content) | 0.1 to 10 | 0.2 to 8.0 | 0.5 to 7.0 | 0.6 to 4.0 | 0.7 to 5.0 |
| BALANCE ® RCF (specifications as solids content) | 0.1 to 10 | 0.2 to 8.0 | 0.5 to 7.0 | 0.6 to 4.0 | 0.7 to 5.0 |
| Vinylpyrrolidone/ Vinylacetate-Copolymer | 1.0 to 10 | 2.0 to 8.5 | 2.0 to 8.5 | 3.0 to 7.0 | 3.0 to 7.0 |
| Water | 50 to 95 | 50 to 95 | 60 to 90 | 60 to 90 | 65 to 85 |
| Misc | add 100 | add 100 | add 100 | add 100 | add 100 |

|  | Formula 41 | Formula 42 | Formula 43 | Formula 44 | Formula 45 |
|---|---|---|---|---|---|
| Copolymer a) | 0.1 to 10 | 0.2 to 8.0 | 0.5 to 7.0 | 0.6 to 4.0 | 0.7 to 5.0 |
| Copolymer b) | 0.1 to 10 | 0.2 to 8.0 | 0.5 to 7.0 | 0.6 to 4.0 | 0.7 to 5.0 |
| Carbomer | 0.02 to 3.0 | 0.05 to 2.0 | 0.05 to 1.5 | 0.2 to 1.0 | 0.4 to 0.8 |
| Water | 50 to 95 | 50 to 95 | 60 to 90 | 60 to 90 | 65 to 85 |
| Misc | add 100 | add 100 | add 100 | add 100 | add 100 |

|  | Formula 41a | Formula 42a | Formula 43a | Formula 44a | Formula 45a |
|---|---|---|---|---|---|
| Acrylates Copolymer | 0.1 to 10 | 0.2 to 8.0 | 0.5 to 7.0 | 0.6 to 4.0 | 0.7 to 5.0 |
| Acrylates/Ceteareth-20 Methacrylate Crosspolymer | 0.1 to 10 | 0.2 to 8.0 | 0.5 to 7.0 | 0.6 to 4.0 | 0.7 to 5.0 |
| Carbomer | 0.02 to 3.0 | 0.05 to 2.0 | 0.05 to 1.5 | 0.2 to 1.0 | 0.4 to 0.8 |
| Water | 50 to 95 | 50 to 95 | 60 to 90 | 60 to 90 | 65 to 85 |
| Misc | add 100 | add 100 | add 100 | add 100 | add 100 |

|  | Formula 41b | Formula 42b | Formula 43b | Formula 44b | Formula 45b |
|---|---|---|---|---|---|
| Aculyn ® 33A (specifications as solids content) | 0.1 to 10 | 0.2 to 8.0 | 0.5 to 7.0 | 0.6 to 4.0 | 0.7 to 5.0 |
| BALANCE ® RCF (specifications as solids content) | 0.1 to 10 | 0.2 to 8.0 | 0.5 to 7.0 | 0.6 to 4.0 | 0.7 to 5.0 |
| Carbomer | 0.02 to 3.0 | 0.05 to 2.0 | 0.05 to 1.5 | 0.2 to 1.0 | 0.4 to 0.8 |
| Water | 50 to 95 | 50 to 95 | 60 to 90 | 60 to 90 | 65 to 85 |
| Misc | add 100 | add 100 | add 100 | add 100 | add 100 |

-continued

|  | Formula 46 | Formula 47 | Formula 48 | Formula 49 | Formula 50 |
| --- | --- | --- | --- | --- | --- |
| Copolymer a) | 0.1 to 10 | 0.2 to 8.0 | 0.5 to 7.0 | 0.6 to 4.0 | 0.7 to 5.0 |
| Copolymer b) | 0.1 to 10 | 0.2 to 8.0 | 0.5 to 7.0 | 0.6 to 4.0 | 0.7 to 5.0 |
| PEG-40 Hydrogenated Castor Oil | 0.05 to 1.5 | 0.1 to 1.0 | 0.2 to 0.9 | 0.3 to 0.8 | 0.4 to 0.6 |
| Water | 50 to 95 | 50 to 95 | 60 to 90 | 60 to 90 | 65 to 85 |
| Misc | add 100 | add 100 | add 100 | add 100 | add 100 |

|  | Formula 46a | Formula 47a | Formula 48a | Formula 49a | Formula 50a |
| --- | --- | --- | --- | --- | --- |
| Acrylates Copolymer | 0.1 to 10 | 0.2 to 8.0 | 0.5 to 7.0 | 0.6 to 4.0 | 0.7 to 5.0 |
| Acrylates/Ceteareth-20 Methacrylate Crosspolymer | 0.1 to 10 | 0.2 to 8.0 | 0.5 to 7.0 | 0.6 to 4.0 | 0.7 to 5.0 |
| PEG-40 Hydrogenated Castor Oil | 0.05 to 1.5 | 0.1 to 1.0 | 0.2 to 0.9 | 0.3 to 0.8 | 0.4 to 0.6 |
| Water | 50 to 95 | 50 to 95 | 60 to 90 | 60 to 90 | 65 to 85 |
| Misc | add 100 | add 100 | add 100 | add 100 | add 100 |

|  | Formula 46b | Formula 47b | Formula 48b | Formula 49b | Formula 50b |
| --- | --- | --- | --- | --- | --- |
| Aculyn ® 33A (specifications as solids content) | 0.1 to 10 | 0.2 to 8.0 | 0.5 to 7.0 | 0.6 to 4.0 | 0.7 to 5.0 |
| BALANCE ® RCF (specifications as solids content) | 0.1 to 10 | 0.2 to 8.0 | 0.5 to 7.0 | 0.6 to 4.0 | 0.7 to 5.0 |
| PEG-40 Hydrogenated Castor Oil | 0.05 to 1.5 | 0.1 to 1.0 | 0.2 to 0.9 | 0.3 to 0.8 | 0.4 to 0.6 |
| Water | 50 to 95 | 50 to 95 | 60 to 90 | 60 to 90 | 65 to 85 |
| Misc | add 100 | add 100 | add 100 | add 100 | add 100 |

In the context of the present disclosure, "Misc" is understood to mean a cosmetic carrier, for example water (unless indicated separately) and optionally additional conventional components of styling products.

The cosmetic composition of the present disclosure can be packed in the conventional forms for the temporary shaping of hair, such as hair gel, hairspray, mousse or hair wax. Packaging as hair gel is optional.

Hair mousse and hairsprays may have the presence of propellants. As contemplated herein, however, these propellants might not contain any or only minor quantities of hydrocarbons. Propane, propane/butane mixtures and dimethyl ether are suitable propellants as contemplated herein.

The present disclosure also relates to the use of cosmetic composition claimed for the temporary shaping of keratinous fibers, such as of human hair, as well as a method for the temporary shaping of keratinous fibers, such as human hair, wherein the cosmetic composition claimed is applied on keratinous fibers.

An additional subject of this disclosure is the use of a cosmetic composition as contemplated herein for the improvement of the hold of temporarily shaped keratinous fibers.

EXAMPLES

The following hair gels were produced:

| Component/raw material | INCI designation or chemical name | V1 | V2 | E1 |
| --- | --- | --- | --- | --- |
| Aculyn ® 33A [1] | Acrylates/Neodecanoate Crosspolymer | 3.5 | — | 1.75 |
| BALANCE ® RCF [2] | Acrylates/Ceteareth-20 Methacrylate Crosspolymer | — | 3.3 | 1.65 |

-continued

| Component/raw material | INCI designation or chemical name | V1 | V2 | E1 |
| --- | --- | --- | --- | --- |
| AMP-ULTRA PC 2000 | Aminomethyl Propanol | 0.3 | 0.3 | 0.3 |
| Water |  | 96.2 | 96.4 | 96.3 |
| Total |  | 100 | 100 | 100 |

[1] 27.5 wt. % of active substance in water
[2] 30 wt. % of active substance in water The quantity specifications in the table specified as wt. % of the respective raw material, relative to the total composition. The polymer content in each of the compositions V1, V2 and E1 was 1.0 wt. %.

The maximum hold (N) was determined for the produced styling agents by employing a 3PB test (3-point bending test) on cleaned Kerling hair strands (mean value of 5 hair strands each):

|  | V1 | V2 | E1 |
| --- | --- | --- | --- |
| Fmax | 2.0 | 2.4 | 2.9 |

The polymer combination E1 as contemplated herein demonstrated a clear overadditive, synergistic effect with regard to the maximum hold.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the various embodiments in any way. Rather, the foregoing detailed description will provide those skilled in the art with a convenient road map for implementing an exemplary embodiment as contemplated herein. It being understood that various changes may be made in the function and arrangement of elements described in an exemplary embodiment without departing from the scope of the various embodiments as set forth in the appended claims.

The invention claimed is:

1. A cosmetic composition for the temporary shaping of hair consisting of:
   a) from 0.5 to 7.0 wt. % by weight of Acrylates/Neodecanoate cross polymer
   b) from 0.5 to 7.0 wt. % by weight of Acrylates/Ceteareth-20 methacrylate cross polymer;
   (c) water,
   (d) 2-amino-2-methylpropanol
   e) optionally a film-forming polymer different from copolymer (a) and different from copolymer (b) and
   f) optionally emulsifier or a surfactant.

2. Cosmetic composition according to claim 1, wherein the amount of water is 50-95 wt %.

3. Method for the temporary shaping of hair where the cosmetic composition according to claim 1 is applied on to hair.

4. Cosmetic composition according to claim 2, wherein the amount of water is between 65-85 wt %.

5. Cosmetic composition according to claim 1, wherein the film-forming polymer is homopolyacrylic acid and is present in the cosmetic composition from 0.02% to 3% by weight of the overall cosmetic composition.

6. Cosmetic composition according to claim 1, wherein the emulsifier or surfactant is present in the cosmetic composition from 0.05% to 1.5% by weight of the overall cosmetic composition.

7. Cosmetic composition according to claim 1, wherein the amount of 2-amino-2-methylpropanol is 0.1-3 wt %.

* * * * *